United States Patent
Mitsui et al.

[11] 3,989,042
[45] Nov. 2, 1976

[54] OSCILLATOR-EXCITING SYSTEM FOR ULTRASONIC LIQUID NEBULIZER

[75] Inventors: Sadao Mitsui; Minoru Takahashi, both of Tokyo, Japan

[73] Assignee: TDK Electronics Company, Limited, Tokyo, Japan

[22] Filed: May 29, 1975

[21] Appl. No.: 581,904

[30] Foreign Application Priority Data
June 6, 1974   Japan.............................. 49-063341
Sept. 30, 1974 Japan.............................. 49-112568

[52] U.S. Cl. ...................... 128/194; 128/DIG. 2; 239/102; 310/8.1; 331/160
[51] Int. Cl.² ................... A61H 1/00; A61M 15/00
[58] Field of Search ........... 128/194, 173, 186, 193, 128/DIG. 2, 24 A; 239/102, 338; 259/DIG. 44; 261/DIG. 48; 310/8.1; 331/116 R, 158, 160

[56] References Cited
UNITED STATES PATENTS

| | | |
|---|---|---|
| 3,490,697 | 1/1970 | Best, Jr. .......................... 128/DIG. 2 |
| 3,593,712 | 7/1971 | Weaver ............................... 128/194 |
| 3,809,977 | 5/1974 | Balamuth et al. ................. 128/24 A |
| 3,828,773 | 8/1974 | Buch ................................... 128/194 |
| 3,871,395 | 3/1975 | Murray ........................ 259/DIG. 44 |

*Primary Examiner*—Robert W. Michell
*Assistant Examiner*—Lee S. Cohen
*Attorney, Agent, or Firm*—Burgess Ryan and Wayne

[57] ABSTRACT

In an oscillator-exciting system for a ultrasonic liquid nebulizer, a piezo-oscillator element for nebulizing the liquid is electrically connected to a self-exciting oscillating circuit as a constituent element thereof and the circuit is oscillated at that frequency at which the electric impedance of the piezo-oscillator element is inductive. A protective transistor may be connected to a current-bias resistance of the oscillating circuit, which protective transistor may be cut off by a reed switch sensing the exhaustion of the liquid being nebulized and/or by an overcurrent sensing circuit, for ceasing the oscillation in case of liquid exhaustion and/or overcurrent.

4 Claims, 13 Drawing Figures

Fig.2a  Fig.2b
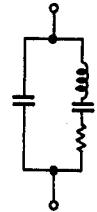
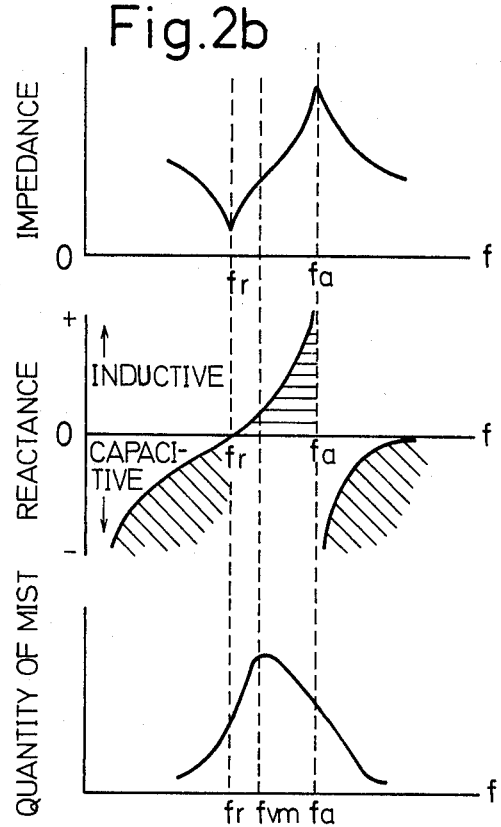
Fig.2c
Fig.2d
Fig.3 PRIOR ART
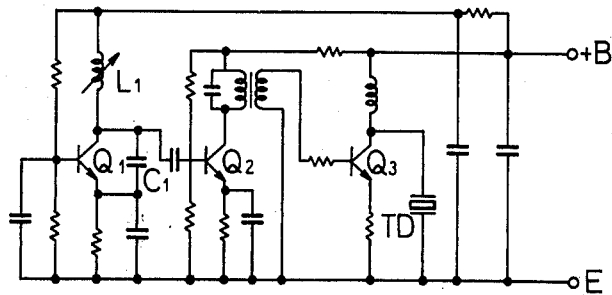

OSCILLATOR-EXCITING SYSTEM FOR ULTRASONIC LIQUID NEBULIZER

BACKGROUND OF THE INVENTION

1. Field of the Invention

This invention relates to a liquid nebulizer which uses ultrasonic waves, and more particularly to an oscillator-exciting system for an ultrasonic liquid nebulizer.

2. Description of the Prior Art

When ultrasonic waves are generated in a liquid and directed to the top surface of the liquid, one or more liquid columns are formed on the top surface, and the liquid is nebulized into a mist-like state from the liquid column. This phenomenon is known, for instance, as disclosed in U.S. Pat. No. 3,387,607, and the phenomenon is used in medical instruments and in room humidifiers. With a conventional liquid nebulizer, a piezo-oscillator element is used for generating the ultrasonic waves, and the piezo-oxcillator element is excited by the output from a separate electric oscillating circuit whose oscillating frequency is determined solely by the constants of various electric parts within the oscillating circuit. The power from the oscillating circuit may be amplified before being applied to the piezo-oscillating element. In such a conventional oscillator-exciting system. the oscillating frequency of the separate oscillating circuit must be adjusted to the optimal frequency of the piezo-oscillator element or, if such adjustment is not possible, a piezo-oscillator element having an optimal frequency which is identical with the output frequency of the separate oscillating circuit must be selected. When the piezo-oscillator element is replaced due to failure or at the end of its service life, the aforesaid adjustment or the selection must be conducted for each replacement. Furthermore, in order to maintain the oscillating frequency at the optimal value regardless of the ambient temperature variation and power source voltage fluctuation, the separate oscillating circuit becomes complicated and expensive.

Therefore, an object of the present invention is to mitigate the aforesaid difficulties of the conventional ultrasonic liquid nebulizer, by providing an improved oscillator-exciting system for an altrasonic liquid nebulizer which system is made of a simple electric circuit and is easy to adjust and maintain.

Another object of the present invention is to provide an oscillator-exciting system for an ultrasonic liquid nebulizer, which system is provided with protective means for ceasing the oscillation in case of exhaustion of the liquid being nebulized and/or in case of excessive overcurrent therethrough.

SUMMARY OF THE INVENTION

To fulfill the aforesaid objects, the oscillator-exciting system for an ultrasonic liquid nebulizer according to the present invention is characterized in that a self-oscillating circuit is formed by using a piezo-oscillator element as a constituent element thereof, so as to excite the piezo-oscillator element by the self-oscillating circuit. The oscillating frequency of the self-oscillating circuit is selected at a suitable value for nebulizing the liquid by the piezo-oscillator element. The frequency suitable for the liquid nebulization is intrinsic to the piezo-oscillator element. The self-oscillating circuit by itself provides a sufficient amount of energy to the piezo-oscillator element for nebulizing the liquid.

The aforesaid self-oscillating circuit may include a transistor to which the piezo-oscillator element is connected as a load thereof, and a current-bias resistance connected between the base of the transistor and a power source potential. In one embodiment of the present invention, a second transistor is included in the self-oscillating circuit in such a manner that at least a part of the currrent-bias resistance is connected to the collector-emitter circuit of the second transistor, and a reed switch is inserted between the base of the second transistor and the reference potential of the self-oscillating circuit. The reed switch is disposed at the bottom of the liquid to be nebulized and it is actuatable by a floating magnet which is placed on the top surface of the liquid being nebulized. Thus, when the liquid is exhausted, the liquid level is lowered together with the floating magnet thereon, so as to actuate the reed switch, for ceasing the excitation of the piezo-oscillator element by cuttinhg off the second transistor. Thus, the oscillator-exciting system is protected from liquid exhaustion.

In another embodiment of the present invention, a second transistor is included in the self-oscillating circuit in such a manner that at least a part of the current-bias resistance is connected to the collector-emitter circuit of the second transistor, and the anode-cathode circuit of a controlled rectifier with a gate is connected between the base of the second transistor and the reference potential of the self-oscillating circuit. A voltage proportional to the magnitude of current through the self-oscillating circuit is applied to the gate of the controlled rectifier, for cutting off the rectifier an ceasing the oscillation of the piezo-oscillator element in case of overcurrent therethrough. Thus, the oscillator-exciting system is protected from excessive overcurrent.

BRIEF DESCRIPTION OF THE DRAWINGS

The invention will now be described in detail by referring to the accompanying drawings, in which:

FIGS. 2a through 2d are diagrammatic illustrations of the operation of a piezo-oscillator element;

FIG. 3 is a circuit diagram of a conventional oscillator-exciting system;

Like parts are designated by like numerals and symbols throughout the different figures.

DESCRIPTION OF THE PREFERRED EMBODIMENTS

Figure 1:
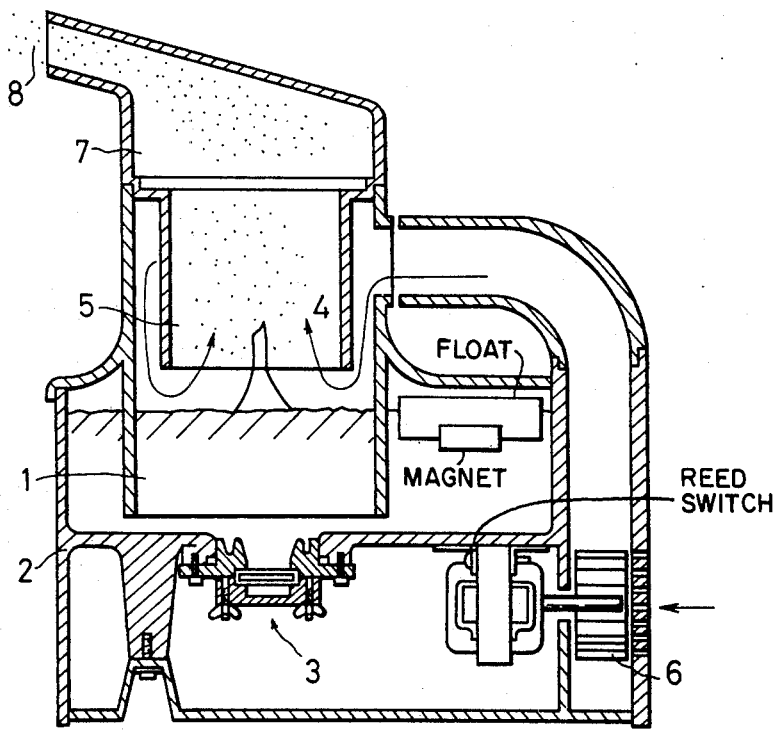
FIG. 1 is a schematic sectional view of a liquid nebulizer, to which an oscillator-exciting system according to the present invention is applied.

FIG. 1 shows a schematic sectional view of a typical liquid nebulizer, e.g., a room humidifier, to which an oscillator-exciting system according to the present invention can be applied. Liquid 1 (i.e., water in the case of the humidifier) is contained in a vessel 2. A nebulizer unit 3 is disposed at the bottom of the vessel 2, which unit includes an oscillator element, i.e., a piezo-oscillator element, and an exciting circuit for the piezo-oscillator element. Upon being excited, the piezo-oscillator element of the nebulizing unit 3 generates ultrasonic waves, for producing a water column 4 on the top surface of the water 1 in the vessel 2. As a result, fine water particles 5 are generated from the water column 4. A fan 6 blows wind so as to bring the fine water particles 5 toward a duct 7 and spread them from an exit 8 into a space to be humidified.

FIGS. 2a through 2d diagrammatically illustrate the operation of the piezo-oscillator element and the optimal frequency of the nebulizing unit 3. FIG. 2a is an electric equivalent circuit of the piezo-oscillator element. Generally speaking, the frequency-impedance characteristics of the equivalent circuit of FIG. 2a has a series resonance frequency $f_r$ and a parallel resonance frequency $f_a$ as shown in FIG. 2b. The reactance of the equivalent circuit of FIG. 2b, i.e., the reactance of the piezo-oscillator element, becomes inductive (namely, positive reactance) at frequencies between the series resonance frequency $f_r$ and the parallel resonance frequency $f_a$, while it becomes capacitive (namely, negative reactance) at other frequencies, as shown in FIG. 2c. FIG. 2d illustrates the relationship between the oscillating frequency of the piezo-oscillator element and the amount of liquid nebulized by the nebulizing unit, as determined by tests, provided that the exciting power of the piezo-oscillator element is constant. As is apparent from FIG. 2d, the optimal frequency $f_{vm}$, in terms of maximizing the amount of the liquid nebulized, is neither the series resonance frequency $f_r$ nor the parallel resonance frequency $f_a$, but is at an intermediate point in the frequency range between $f_r$ and $f_a$ wherein the reactance of the piezo-oscillator element is inductive (namely, the amount of the liquid nebulized is not maximized at the series resonance frequency $f_r$ wherein the amplitude of the vibration of the piezo-oscillator element is maximized).

FIG. 3 shows a circuit diagram of a conventional oscillator-exciting system. In this circuit, three different transistors $Q_1$, $Q_2$ and $Q_3$ perform the functions of oscillation, voltage amplification, and power amplification, respectively. The oscillating frequency is adjusted to the optimal value $f_{vm}$ by regulating a variable coil $L_1$, so as to excite a piezo-oscillator element TD. For instance, in the case nebulizing water, the exciting frequency may be selected in a range of 800 KHz to 2,000 KHz, and a disk-like zircon lead titanate oscillator element of 20–25 mm diameter and 1–2.5 mm thickness may be used, with exciting power of 20–25 W. However, the circuit of FIG. 3 has a shortcoming in that it is separately excited and that the circuit is complicated, as pointed out in the foregoing.

Figure 4A:
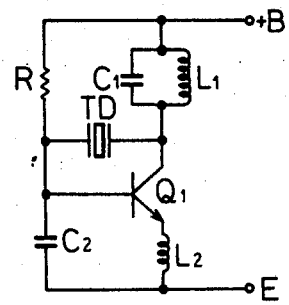
FIGS. 4a, 4b, 4c and 4d are basic circuit diagram of four different basic formations of the oscillator-exciting system, according to the present invention.
Figure 4C:
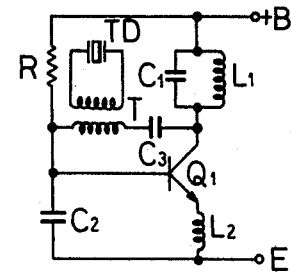

FIGS. 4a, 4b, 4c and 4d illustrates four different basic formations of the oscillator-exciting system according to the present invention. In each of the figures, the symbols +B, E, Q, and TD represent power source voltage, reference voltage a transistor, and a piezo-oscillator element, respectively. In FIG. 4a and FIG. 4c, a current-bias resistor R is connected between the power source +B and the base of the transistor Q. The formation of FIG. 4a is based on the Colpitts oscillating circuit, and the resonance frequency $f_o$ of parallel resonance circuit having a capacitance $C_1$ and an inductance $L_1$ is designed to be lower than the optimal frequency $f_{vm}$ of FIG. 2d. Accordingly, the aforesaid parallel resonance circuit becomes capacitive at the optimal frequency $f_{vm}$. To cause the circuit of FIG. 4a to act as a Colpitts oscillating circuit when the oscillator element TD is inductive, and inductance $L_2$ and a capacitance $C_2$ are set so as to satisfy the conditions of $2\pi f_{vm} L_2 << 2\pi f_{vm} C_2$. Thus, this circuit does not oscillate at such frequencies which make the piezo-oscillator element TD capacitive. The inductance $L_2$ is inserted for improving the stability of the oscillation and can also be inserted in the base circuit of the transistor $Q_1$.

Figure 4B:
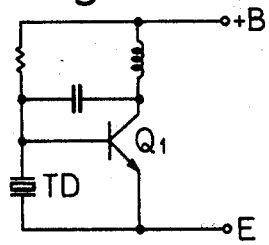

FIG. 4b illustrates another basic formation of the oscillator-exciting system according to the present invention, which is based on the Hartley oscillating circuit.

FIG. 4c shows a modification of the formation of FIG. 4a, which modification includes a transformer T connected between the piezo-oscillator element TD and the oscillating circuit, for establishing the impedance matching. Accordingly, the modification improves the efficiency of the oscillating circuit.

Figure 4D:
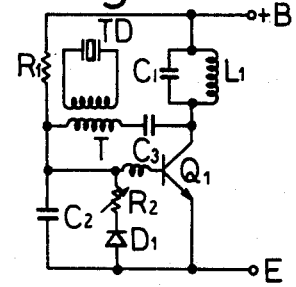

FIG. 4d shows another modification, in which a base current of the transistor $Q_1$ is supplied by rectifying a part of the oscillated high frequency current. In this embodiment, the power consumed in the bias resistors $R_1$ and $R_2$ is quite small and, thus, a small potentiometer $R_2$ can adjust the quantity of the mist. Therefore, the embodiment of FIG. 4d is very beneficial both in economical and functional aspects.

Figure 5:
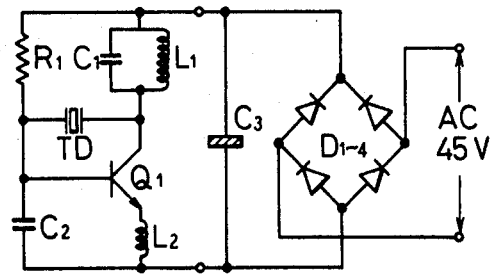
FIG. 5 is a circuit diagram of a practical oscillator-exciting system, according to the present invention.

FIG. 5 illustrates a circuit diagram of a practical oscillator-exciting system based on the formation of FIG. 4a, according to the present invention. The input voltage to the circuit of FIG. 5 is AC 45 V, which is converted into a DC voltage by diodes $D_1$ through $D_4$ and a capacitor $C_3$ for actuating the oscillating circuit of the system. Various constants of the circuit of FIG. 5 and the operating characteristics thereof, as determined by tests, are as follows.

| | |
|---|---|
| Resistance $R_1$: | 1 KΩ |
| Capacitance $C_1$: | 1,200 pF |
| Capacitance $C_2$: | 0.03 μF |
| Capacitance $C_3$: | 10 μF |
| Inductance $L_1$: | 22 μH |
| Inductance $L_2$: | 0.19 μH |
| Transistor $Q_1$: | 2SC940 |
| Diodes $D_1$-$D_4$: | V03C |
| Piezo-Oscillator element: | |
| Material; | Zircon lead titanate |
| Outer diameter; | 20 mm |
| Thickness; | 1.25 mm |
| Counterelectrode diameter; | 13 mm |
| Coupling factor; | 62% |
| Resonance impedance; | 4 Ω |
| Input voltage: | AC 45 V |
| Input current: | 0.69 A |
| Oscillating frequency: | 1.677 MHz |
| Nebulizing ability (water): | 440 cc/hour |

With the embodiment of the present invention, as illustrated in FIGS. 4 and 5, a piezo-oscillator element is used as a constituent element of a self-oscillating circuit, so as to complete the self-oscillating circuit with only one transistor. Thus, the construction of the oscillating circuit is considerably simplified, and the manufacturing cost of the nebulizing unit can be reduced. In addition, the oscillating frequency of the oscillating circuit is selected not at the maximum amplitude frequency but at a frequency wherein the impedance of the piezo-oscillator element is inductive, so that the nebulizing ability is greatly improved. It is one of the important characteristics of the present invention to select that oscillating frequency which keeps the piezo-oscillator element inductive. Furthermore, once being properly set, the oscillator-exciting system according to the present invention does not require any adjustment, so that it is highly stable in terms of the temperature characteristics, the aging, and the response to power source voltage fluctuation.

For some applications, it may be desirable to incorporate protective functions in the oscillator-exciting system; namely, a function of automatically ceasing the oscillation in case of the liquid exhaustion in the vessel 2, and a function of automatically interrupting the operation of the oscillating circuit when the piezo-oscillator element is accidentally disconnected from the oscillating circuit (this disconnection may occur during circuit adjustment or circuit failure) in order to protect the circuit from overloading.

Figure 6:
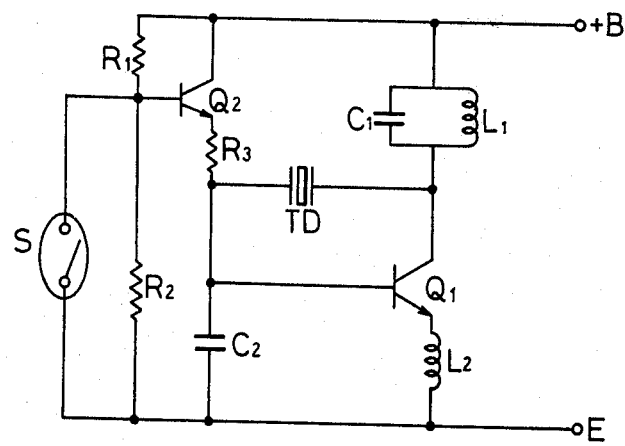
FIGS. 6 and 7 are circuit diagrams of two modifications of the oscillator-exciting system of FIG. 5 by adding protective means therein.

FIG. 6 shows another embodiment of the present invention, which includes a protective means against liquid exhaustion. In comparison with the basic formation of FIG. 4a, the embodiment of FIG. 6 is characterized in that the collector-emitter circuit of a second transistor $Q_2$ is connected in series with at least a part of the current-bias resistance R between the power source and the base of the first transistor $Q_1$, and a reed switch S is connected between the base of the second transistor $Q_2$ and the reference potential E. More particularly, resistances $R_1$ and $R_2$ are connected in series, and the two resistances thus connected are inserted between the power source potential +B and the reference potential E, while the junction of these two resistances is connected to the base of the second transistor $Q_2$. The collector of the second transistor $Q_2$ is directly connected to the power source potential +B, while the emitter of the transistor $Q_2$ is connected to one end of a resistance $R_3$. The opposite end of the resistance $R_3$ is connected to the junction of one end of the piezo-oscillator element TD, the base of the first transistor $Q_1$, and one end of the capacitance $C_2$, in the same manner as in the circuit of FIG. 4a.

The reed switch S cooperates with a float magnet (not shown) which floats on the top surface of the liquid 1 in the vessel 2 of the nebulizer (FIG. 1). As the amount of the liquid 1 is reduced by nebulization, the top level of the liquid is gradually lowered, until the float magnet approaches the reed switch S (FIG. 6) which is disposed in the proximity of the bottom of the vessel. When the float magnet comes into a predetermined distance from the reed switch S in response to the liquid consumption, the reed switch is closed. As a result, the bias voltage of the second transistor $Q_2$ becomes zero, and the transistor $Q_2$ is cut off. Then, the DC bias to the first transistor $Q_1$ is removed, and the oscillation by the transistor $Q_1$ is ceased.

Thus, with the circuit of FIG. 6, when the liquid 1 in the vessel 2 is exhausted, the oscillation is automatically stopped. The reason for using the second transistor $Q_2$ in conjunction with the reed switch S is that there is not any suitable portion in the circuit of FIG. 4a for directly inserting the closeable electric contacts of the reed switch S.

The circuit of FIG. 6 has another advantage that the amount of the nebulized liquid can be economically controlled by regulating the intensity of the oscillation. If the control of the amount of the nebulized liquid is desired in the circuit of FIG. 4a, the current-bias resistance R should be made variable wherein a large amount energy is consumed as a loss. On the other hand, in the case of the circuit of FIG. 6, the resistance $R_2$ can be made variable for controlling the amount of the nebulized liquid, and the power loss in the resistance $R_2$ is small. Under certain conditions, the loss in the current-bias resistance R is about 25 W, while the loss in the resistance $R_2$ is only 0.1 W.

Figure 7:
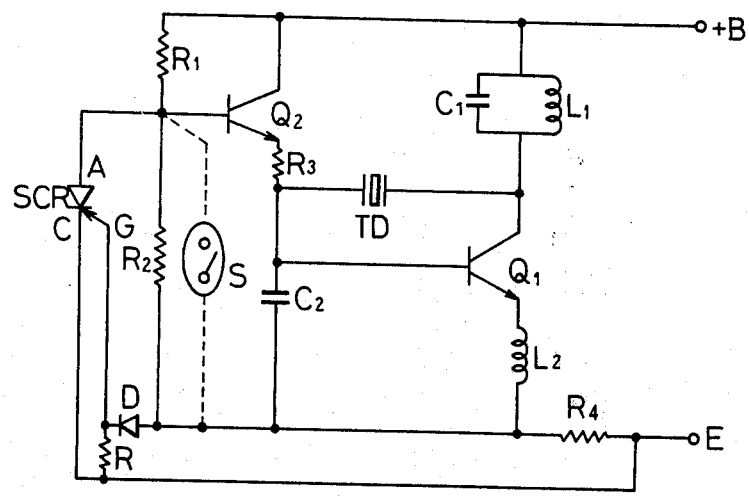

FIG. 7 shows a circuit diagram of another embodiment of the oscillator-exciting system according to the present invention. In comparison with the circuit of FIG. 6, the embodiment of FIG. 7 is characterized in that a silicon controlled rectifier SCR is included in such a manner that the circuit from the anode A to the cathode C of the SCR is connected between the base of the second transistor $Q_2$ and the reference potential E, and a voltage proportional to the input current to the oscillating circuit is applied to the gate of the SCR through a resistance $R_4$. With the circuit of FIG. 7, as long as the operation of the oscillator-exciting system is normal, the silicon controlled rectifier SCR is kept cut off. However, if an excessively large current flows through the oscillating circuit, the voltage drop across the resistance $R_4$ becomes large, and the voltage at the gate G becomes high enough for turning the SCR on. As a result, the base voltage of the second transistor $Q_2$ becomes equal to the reference potential, so that the second transistor $Q_2$ is cut off and the oscillation by the first transistor $Q_1$ is ceased. Such an excessively large current through the oscillating circuit is caused, for instance, when the piezo-oscillator element TD is removed from the circuit, and if such a condition is sustained, the circuit does not oscillated and the bias voltage of the first transistor $Q_1$ becomes very high and the collector current of the transistor $Q_1$ becomes excessively large and the transistor $Q_1$ may be damaged. This kind of fault tends to occur when the piezo-oscillator element TD is connected to the oscillating circuit by cables with connectors. The embodiment of FIG. 7 completely eliminates such faults.

It should be noted here that the embodiment of FIG. 7 also includes the reed switch S, which has been described in detail hereinbefore with reference to FIG. 6, so that the embodiment of FIG. 7 fulfills both the protection against the liquid exhaustion and the protection against overcurrent.

As is apparent from the foregoing disclosure, with the embodiments of FIGS. 6 and 7, the oscillation is automatically ceased when the liquid being nebulized is exhausted and/or when an overcurrent fault occurs in the oscillating circuit. Whereby, the oscillator-exciting system is protected from damages due to loss of load and/or fault.

What we claim is:
1. An oscillator-exciting system for an ultrasonic liquid nebulizer comprising a vessel containing liquid, a power source providing an electrical potential, a piezo-oscillator element disposed in said vessel, and a self-oscillating electric circuit connected across said power source potential and a reference potential, said self-oscillating circuit having said piezo-oscillator element connected thereto as a constituent element thereof, said oscillating circuit being adapted to oscillate at that frequency in which the electric impedance of said piezo-oscillator element is inductive, so as to nebulize the liquid by the oscillation of the piezo-oscillator element, said self-oscillating circuit including an oscillating transistor and a current-bias resistance connected between a base of the transistor and said power source potential, a second transistor having a collector-emitter circuit connected in series with at least a part of said current-bias resistance, a float magnet floating on the top surface of said liquid, and a reed switch disposed at the bottom of said vessel and aligned with said float magnet so as to be actuated by said float magnet in response to a lowering of the liquid below a predetermined level, said reed switch being connected between a base of said second transistor and said reference potential.

2. An oscillator-exciting system for a ultrasonic liquid nebulizer, comprising a vessel containing liquid, a power source providing an electrical potential, a piezo-oscillator element disposed in said vessel, and a self-oscillating electric circuit connected across said power source potential and a reference potential, said self-oscillating circuit having said piezo-oscillator element connected thereto as a constituent element thereof, said oscillating circuit being adapted to oscillate at that frequency in which the electric impedance of said piezo-oscillator element is inductive, so as to nebulize the liquid by the oscillation of the piezo-oscillator element, said self-oscillating circuit including an oscillating transistor and a current-bias resistance connected between a base of the transistor and said power source potential, a second transistor having a collector emitter circuit connected in series with at least a part of said current-bias resistance, a controlled rectifier having an anode-cathode circuit thereof connected between a base of said second transistor and said reference potential, and a means producing a voltage proportional to the load current of said self-oscillating circuit, said controlled rectifier having a gate connected to said voltage producing means so as to receive said voltage proportional to the load current for providing a low impedance path through said anode-cathode circuit in response to said load current exceeding a predetermined limit.

3. An oscillator-exciting system for an ultrasonic liquid nebulizer, comprising a vessel containing liquid, a power source providing an electrical potential, a piezo-oscillator element disposed in said vessel, and a self-oscillating electric circuit connected across said power source potential and a reference potential, said self-oscillating circuit having said piezo-oscillator element connected thereto as a constituent element thereof, said oscillating circuit being adapted to oscillate at that frequency in which the electric impedance of said piezo-oscillator element is inductive, so as to nebulize the liquid by the oscillation of the piezo-oscillator element, said self-oscillating circuit including an oscillating transistor and a current-bias resistance connected between the base of the transistor and said power source potential, a second transistor having a collector-emitter circuit connected in series with at least a part of said current-bias resistance, a float magnet floating on the top surface of said liquid, a reed switch disposed at the bottom of said vessel in alignment with said float magnet so as to be actuated by said float magnet in response to a decrease in the liquid level below a predetermined level, said reed switch being connected between a base of said second transistor and said reference potential, a controlled rectifier having an anode-cathode circuit thereof connected between the base of said second transistor and said reference potential, and a means producing a voltage proportional to the load current of said self-oscillating circuit, said controlled rectifier having a gate connected to said means and receiving said voltage proportional to the load current for providing a low impedance path through said anode-cathode circuit in response to said load current exceeding a predetermined limit.

4. An oscillator-exciting system for an ultrasonic liquid nebulizer, comprising a vessel containing liquid, a power source providing an electrical potential, a piezo-oscillator element disposed in said vessel, and a self-oscillating electric circuit connected across said power source potential and a reference potential, said self-oscillating circuit having said piezo-oscillator element connected thereto as a constituent element thereof, said oscillating circuit being adapted to oscillate at that frequency in which the electric impedance of said piezo-oscillator element is inductive, so as to nebulize the liquid by the oscillation of the piezo-oscillator element, a transformer electrically connected between said piezo-oscillator element and said oscillating circuit, said self-oscillating circuit including an oscillating transistor and a current-bias resistance connected between a base of the transistor and said power source potential, a second transistor having a collector-emitter circuit connected in series with at least a part of said current-bias resistance, a float magnet floating on the top surface of said liquid, and a reed switch disposed at the bottom of said vessel in alignment with said float magnet so as to be actuated by said float magnet in response to a lowering of the liquid level below a predetermined level said reed switch being connected betwee a base of said second transistor and said reference potential.

* * * * *

UNITED STATES PATENT OFFICE
CERTIFICATE OF CORRECTION

Patent No. 3,989,042      Dated November 2, 1976

Inventor(s) Sadao Mitsui, et al

It is certified that error appears in the above-identified patent and that said Letters Patent are hereby corrected as shown below:

Column 1, line 27: After "tem" change the period to a comma.

line 45: Change "altrasonic" to --ultrasonic--.

Column 2, line 33: Change "an" to --and--.

Column 3, line 57: Insert a comma after "voltage".

Column 4, line 2: Change "conditions" to --condition--.

Column 6, line 29: Change "oscillated" to --oscillate--.

Column 8, line 4: Change "resitance" to --resistance--.

Signed and Sealed this

Twenty-sixth Day of April 1977

[SEAL]

Attest:

RUTH C. MASON  
*Attesting Officer*

C. MARSHALL DANN  
*Commissioner of Patents and Trademarks*